(12) United States Patent
DiGiore et al.

(10) Patent No.: US 8,649,879 B2
(45) Date of Patent: Feb. 11, 2014

(54) LEADS WITH RETENTION FEATURES FOR SEGMENTED ELECTRODES AND METHODS OF MAKING AND USING THE LEADS

(75) Inventors: Andrew DiGiore, San Francisco, CA (US); Anne Margaret Pianca, Santa Monica, CA (US); Michael Adam Moffitt, Valencia, CA (US)

(73) Assignee: Boston Scientific Neuromodulation Corporation, Valencia, CA (US)

( * ) Notice: Subject to any disclaimer, the term of this patent is extended or adjusted under 35 U.S.C. 154(b) by 0 days.

(21) Appl. No.: 13/368,982

(22) Filed: Feb. 8, 2012

(65) Prior Publication Data
US 2012/0203320 A1 Aug. 9, 2012

Related U.S. Application Data

(60) Provisional application No. 61/440,529, filed on Feb. 8, 2011.

(51) Int. Cl.
*A61N 1/00* (2006.01)

(52) U.S. Cl.
USPC .......................................................... 607/116

(58) Field of Classification Search
USPC ................................................. 607/115–130
See application file for complete search history.

(56) References Cited

U.S. PATENT DOCUMENTS

| 4,602,624 A | 7/1986 | Naples et al. |
| 4,630,611 A | 12/1986 | King |
| 4,744,370 A | 5/1988 | Harris |
| 5,000,194 A | 3/1991 | van den Honert et al. |
| 5,135,001 A | 8/1992 | Sinofsky et al. |
| 5,374,285 A | 12/1994 | Vaiani et al. |
| 5,458,629 A | 10/1995 | Baudino et al. |
| 5,522,874 A | 6/1996 | Gates |
| 5,711,316 A | 1/1998 | Elsberry et al. |

(Continued)

FOREIGN PATENT DOCUMENTS

| EP | 0580928 A1 | 2/1994 |
| EP | 0650694 B1 | 7/1998 |

(Continued)

OTHER PUBLICATIONS

U.S. Appl. No. 13/275,112, filed Oct. 17, 2011.

(Continued)

*Primary Examiner* — Scott Getzow
(74) *Attorney, Agent, or Firm* — Frommer Lawrence & Haug LLP; Bruce E. Black (57) ABSTRACT

One embodiment is a stimulation lead including a lead body comprising a longitudinal surface, a distal end, and a proximal end; and multiple electrodes disposed along the longitudinal surface of the lead body near the distal end of the lead body. The multiple electrodes include multiple segmented electrodes with each of the segmented electrodes having an exterior surface, an interior surface opposite the exterior surface, a proximal end, and a distal end. At least one of the segmented electrodes includes one or more of a) at least one channel formed in the segmented electrode and extending from the proximal end to the distal end of the segmented electrode, b) an arcuate groove formed in at least one of the distal end surface or the proximal end surface, or c) a notch formed in the segmented electrode and extending from the proximal end to the distal end of the segmented electrode.

16 Claims, 9 Drawing Sheets

(56) References Cited

U.S. PATENT DOCUMENTS

| | | |
|---|---|---|
| 5,713,922 A | 2/1998 | King |
| 5,800,350 A | 9/1998 | Coppleson et al. |
| 5,843,148 A | 12/1998 | Gijsbers et al. |
| 5,938,688 A | 8/1999 | Schiff |
| 5,987,361 A | 11/1999 | Mortimer |
| 6,018,684 A | 1/2000 | Bartig et al. |
| 6,134,478 A | 10/2000 | Spehr |
| 6,161,047 A | 12/2000 | King et al. |
| 6,167,311 A | 12/2000 | Rezai |
| 6,322,559 B1 | 11/2001 | Daulton et al. |
| 6,510,347 B2 | 1/2003 | Borkan |
| 6,556,873 B1 | 4/2003 | Smits |
| 6,564,078 B1 | 5/2003 | Marino et al. |
| 6,678,564 B2 | 1/2004 | Ketterl et al. |
| 6,757,970 B1 | 7/2004 | Kuzma et al. |
| 7,027,852 B2 | 4/2006 | Helland |
| 7,047,084 B2 | 5/2006 | Erickson et al. |
| 7,292,890 B2 | 11/2007 | Whitehurst et al. |
| 7,349,736 B2 | 3/2008 | Ostroff et al. |
| 7,489,971 B1 | 2/2009 | Franz |
| 7,584,005 B1 * | 9/2009 | Jain ................ 607/120 |
| 7,668,601 B2 | 2/2010 | Hegland et al. |
| 7,684,873 B2 | 3/2010 | Gerber |
| 7,761,985 B2 | 7/2010 | Hegland et al. |
| 7,809,446 B2 | 10/2010 | Meadows |
| 7,840,188 B2 | 11/2010 | Kurokawa |
| 7,856,707 B2 | 12/2010 | Cole |
| 7,860,570 B2 | 12/2010 | Whitehurst et al. |
| 7,974,705 B2 | 7/2011 | Zdeblick et al. |
| 7,979,140 B2 | 7/2011 | Schulman |
| 8,000,808 B2 | 8/2011 | Hegland et al. |
| 8,019,440 B2 | 9/2011 | Kokones et al. |
| 8,036,755 B2 * | 10/2011 | Franz ................ 607/116 |
| 8,041,309 B2 | 10/2011 | Kurokawa |
| 8,099,177 B2 | 1/2012 | Dahlberg |
| 8,225,504 B2 | 7/2012 | Dye et al. |
| 8,295,944 B2 | 10/2012 | Howard et al. |
| 2002/0156513 A1 | 10/2002 | Borkan |
| 2002/0183817 A1 | 12/2002 | Van Venrooij et al. |
| 2005/0015130 A1 | 1/2005 | Gill |
| 2005/0038489 A1 | 2/2005 | Grill |
| 2005/0171587 A1 | 8/2005 | Daglow et al. |
| 2006/0025841 A1 | 2/2006 | McIntyre |
| 2006/0168805 A1 | 8/2006 | Hegland et al. |
| 2006/0247697 A1 | 11/2006 | Sharma et al. |
| 2007/0150036 A1 | 6/2007 | Anderson |
| 2007/0203546 A1 | 8/2007 | Stone et al. |
| 2008/0103580 A1 | 5/2008 | Gerber |
| 2008/0114230 A1 | 5/2008 | Addis |
| 2008/0215125 A1 * | 9/2008 | Farah et al. ........ 607/116 |
| 2009/0187222 A1 | 7/2009 | Barker |
| 2009/0204192 A1 | 8/2009 | Carlton et al. |
| 2009/0204193 A1 | 8/2009 | Kokones et al. |
| 2009/0276021 A1 | 11/2009 | Meadows |
| 2010/0036468 A1 | 2/2010 | Decre et al. |
| 2010/0076535 A1 | 3/2010 | Pianca et al. |
| 2010/0082076 A1 | 4/2010 | Lee et al. |
| 2010/0094387 A1 | 4/2010 | Pianca et al. |
| 2010/0268298 A1 | 10/2010 | Moffitt et al. |
| 2010/0269337 A1 | 10/2010 | Dye et al. |
| 2011/0005069 A1 | 1/2011 | Pianca |
| 2011/0047795 A1 | 3/2011 | Turner et al. |
| 2011/0056076 A1 | 3/2011 | Hegland et al. |
| 2011/0078900 A1 | 4/2011 | Pianca et al. |
| 2011/0130803 A1 | 6/2011 | McDonald |
| 2011/0130816 A1 | 6/2011 | Howard et al. |
| 2011/0130817 A1 | 6/2011 | Chen |
| 2011/0130818 A1 | 6/2011 | Chen |
| 2011/0131808 A1 | 6/2011 | Gill |
| 2011/0238129 A1 | 9/2011 | Moffitt et al. |
| 2011/0313500 A1 | 12/2011 | Barker et al. |
| 2012/0016378 A1 | 1/2012 | Pianca et al. |
| 2012/0046710 A1 | 2/2012 | DiGiore et al. |
| 2012/0071949 A1 | 3/2012 | Pianca et al. |

FOREIGN PATENT DOCUMENTS

| | | |
|---|---|---|
| EP | 0832667 B1 | 2/2004 |
| EP | 1181947 B1 | 1/2006 |
| EP | 1848496 B1 | 10/2007 |
| EP | 2092952 A1 | 8/2009 |
| WO | 9732628 A1 | 9/1997 |
| WO | 9955411 A3 | 2/2000 |
| WO | 0038574 A1 | 7/2000 |
| WO | 02068042 A1 | 9/2002 |
| WO | 2004045707 A1 | 6/2004 |
| WO | 2008053789 A1 | 5/2008 |
| WO | 2009025816 A1 | 2/2009 |
| WO | 2009102536 A1 | 8/2009 |

OTHER PUBLICATIONS

U.S. Appl. No. 13/363,059, filed Jan. 31, 2012.
U.S. Appl. No. 13/369,013, filed Feb. 8, 2012.
U.S. Appl. No. 13/368,733, filed Feb. 8, 2012.
U.S. Appl. No. 12/177,823, filed Jul. 22, 2008.
U S. Appl. No. 13/787,171, filed Mar. 6, 2013.
U.S. Appl. No. 13/750,725, filed Jan. 25, 2013.
International Search Report and Written Opinion, International Application No. PCT/US2012/024298, mailed Jun. 6, 2012.
U.S. Appl. No. 13/899,316, filed May 21, 2013.
U.S. Appl. No. 13/906,776, filed May 31, 2013.
U.S. Appl. No. 13/951,057, filed Jul. 25, 2013.

* cited by examiner

LEADS WITH RETENTION FEATURES FOR SEGMENTED ELECTRODES AND METHODS OF MAKING AND USING THE LEADS

CROSS-REFERENCE TO RELATED APPLICATIONS

This application claims the benefit under 35 U.S.C. §119 (e) of U.S. Provisional Patent Application Ser. No. 61/440,529 filed on Feb. 8, 2011, which is incorporated herein by reference.

FIELD

The invention is directed to the area of electrical stimulation systems and leads and methods of making and using the systems and leads. The present invention is also directed to electrical stimulation leads with segmented electrodes having internal retention features, as well as methods of making and using the segmented electrodes, leads, and electrical stimulation systems.

BACKGROUND

Electrical stimulation can be useful for treating a variety of conditions. Deep brain stimulation can be useful for treating, for example, Parkinson's disease, dystonia, essential tremor, chronic pain, Huntington's Disease, levodopa-induced dyskinesias and rigidity, bradykinesia, epilepsy and seizures, eating disorders, and mood disorders. Typically, a lead with a stimulating electrode at or near a tip of the lead provides the stimulation to target neurons in the brain. Magnetic resonance imaging ("MRI") or computerized tomography ("CT") scans can provide a starting point for determining where the stimulating electrode should be positioned to provide the desired stimulus to the target neurons.

After the lead is implanted into a patient's brain, electrical stimulus current can be delivered through selected electrodes on the lead to stimulate target neurons in the brain. Typically, the electrodes are formed into rings disposed on a distal portion of the lead. The stimulus current projects from the ring electrodes equally in every direction. Because of the ring shape of these electrodes, the stimulus current cannot be directed to one or more specific positions around the ring electrode (e.g., on one or more sides, or points, around the lead). Consequently, undirected stimulation may result in unwanted stimulation of neighboring neural tissue, potentially resulting in undesired side effects.

BRIEF SUMMARY

One embodiment is a stimulation lead including a lead body comprising a longitudinal surface, a distal end, and a proximal end; and multiple electrodes disposed along the longitudinal surface of the lead body near the distal end of the lead body. The multiple electrodes include multiple segmented electrodes with each of the segmented electrodes having an exterior surface, an interior surface opposite the exterior surface, a proximal end, and a distal end. At least one of the segmented electrodes includes at least one channel formed in the segmented electrode and extending from the proximal end to the distal end of the segmented electrode.

Another embodiment is a stimulation lead including a lead body comprising a longitudinal surface, a distal end, and a proximal end; and multiple electrodes disposed along the longitudinal surface of the lead body near the distal end of the lead body. The multiple electrodes include multiple segmented electrodes with each of the segmented electrodes having an exterior surface, an interior surface opposite the exterior surface, a proximal end, and a distal end. At least one of the segmented electrodes includes an arcuate groove formed in at least one of the distal end surface or the proximal end surface.

Yet another embodiment is a stimulation lead including a lead body comprising a longitudinal surface, a distal end, and a proximal end; and multiple electrodes disposed along the longitudinal surface of the lead body near the distal end of the lead body. The multiple electrodes include multiple segmented electrodes with each of the segmented electrodes having an exterior surface, an interior surface opposite the exterior surface, a proximal end, and a distal end. At least one of the segmented electrodes includes a notch formed in the segmented electrode and extending from the proximal end to the distal end of the segmented electrode.

A further embodiment is a method of making a stimulation lead that includes disposing at least one pre-electrode along a longitudinal surface of a lead body near a distal end of the lead body. The at least one pre-electrode includes multiple segmented electrodes with each of the segmented electrodes having an exterior surface, an interior surface opposite the exterior surface, a proximal end, and a distal end. At least one of the segmented electrodes has at least one channel, at least one notch, or a combination thereof formed in the segmented electrode and extending from the proximal end to the distal end of the segmented electrode. The method further includes inserting non-conductive material into the at least one channel; and reflowing the non-conductive material within the at least one channel to facilitate retention of the segmented electrode with the stimulation lead.

BRIEF DESCRIPTION OF THE DRAWINGS

Non-limiting and non-exhaustive embodiments of the present invention are described with reference to the following drawings. In the drawings, like reference numerals refer to like parts throughout the various figures unless otherwise specified.

For a better understanding of the present invention, reference will be made to the following Detailed Description, which is to be read in association with the accompanying drawings, wherein.

DETAILED DESCRIPTION

The invention is directed to the area of electrical stimulation systems and methods of making and using the systems. The present invention is also directed to forming electrical stimulation leads with multiple sets of segmented electrodes, as well as methods of making and using the segmented electrodes, leads, and electrical stimulation systems.

A lead for deep brain stimulation may include stimulation electrodes, recording electrodes, or a combination of both. At least some of the stimulation electrodes, recording electrodes, or both are provided in the form of segmented electrodes that extend only partially around the circumference of the lead. These segmented electrodes can be provided in sets of electrodes, with each set having electrodes radially distributed about the lead at a particular longitudinal position.

A practitioner may determine the position of the target neurons using the recording electrode(s) and then position the stimulation electrode(s) accordingly without removal of a recording lead and insertion of a stimulation lead. In some embodiments, the same electrodes can be used for both recording and stimulation. In some embodiments, separate leads can be used; one with recording electrodes which identify target neurons, and a second lead with stimulation electrodes that replaces the first after target neuron identification. A lead may include recording electrodes spaced around the circumference of the lead to more precisely determine the position of the target neurons. In at least some embodiments, the lead is rotatable so that the stimulation electrodes can be aligned with the target neurons after the neurons have been located using the recording electrodes. For illustrative purposes, the leads are described herein relative to use for deep brain stimulation, but it will be understood that any of the leads can be used for applications other than deep brain stimulation.

Deep brain stimulation devices and leads are described in, for example, U.S. Pat. No. 7,809,446 ("Devices and Methods For Brain Stimulation"), U.S. Patent Application Publication No. 2010/0076535 A1 ("Leads With Non-Circular-Shaped Distal Ends For Brain Stimulation Systems and Methods of Making and Using"), U.S. Patent Application Publication 2007/0150036 A1 ("Stimulator Leads and Methods For Lead Fabrication"), U.S. patent application Ser. No. 12/177,823 ("Lead With Transition and Methods of Manufacture and Use"), U.S. Patent Application Publication No. 2009/0276021 A1 ("Electrodes For Stimulation Leads and Methods of Manufacture and Use"), U.S. Patent Application Ser. No. 61/170,037 ("Deep Brain Stimulation Current Steering with Split Electrodes"), U.S. Patent Application Ser. No. 61/022,953, U.S. Patent Application Ser. No. 61/316,759, and U.S. Patent Application Publication No. 2009/0187222 A1. Each of these references is incorporated herein by reference.

Figure 1:
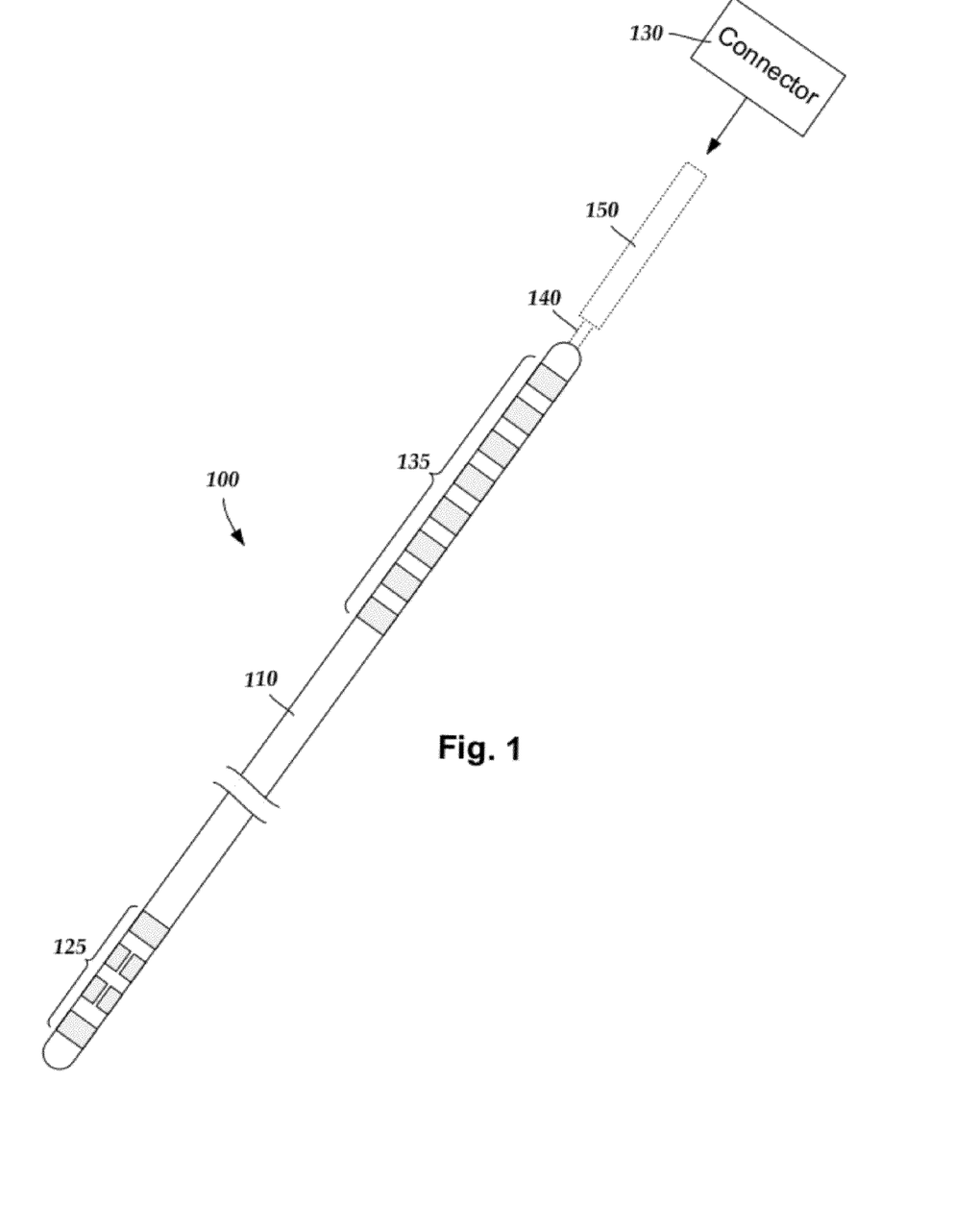
FIG. 1 is a schematic side view of one embodiment of a device for brain stimulation, according to the invention.

FIG. 1 illustrates one embodiment of a device 100 for brain stimulation. The device includes a lead 110, a plurality of electrodes 125 disposed at least partially about a circumference of the lead 110, a plurality of terminals 135, a connector 130 for connection of the electrodes to a control unit, and a stylet 140 for assisting in insertion and positioning of the lead in the patient's brain. The stylet 140 can be made of a rigid material. Examples of suitable materials for the stylet include, but are not limited to, tungsten, stainless steel, and plastic. The stylet 140 may have a handle 150 to assist insertion into the lead 110, as well as rotation of the stylet 140 and lead 110. The connector 130 fits over a proximal end of the lead 110, preferably after removal of the stylet 140.

The control unit (not shown) is typically an implantable pulse generator that can be implanted into a patient's body, for example, below the patient's clavicle area. The pulse generator can have eight stimulation channels which may be independently programmable to control the magnitude of the current stimulus from each channel. In some cases the pulse generator may have more than eight stimulation channels (e.g., 16-, 32-, or more stimulation channels). The control unit may have one, two, three, four, or more connector ports, for receiving the plurality of terminals 135 at the proximal end of the lead 110.

In one example of operation, access to the desired position in the brain can be accomplished by drilling a hole in the patient's skull or cranium with a cranial drill (commonly referred to as a burr), and coagulating and incising the dura mater, or brain covering. The lead 110 can be inserted into the cranium and brain tissue with the assistance of the stylet 140. The lead 110 can be guided to the target location within the brain using, for example, a stereotactic frame and a microdrive motor system. In some embodiments, the microdrive motor system can be fully or partially automatic. The microdrive motor system may be configured to perform one or more the following actions (alone or in combination): insert the lead 110, retract the lead 110, or rotate the lead 110.

In some embodiments, measurement devices coupled to the muscles or other tissues stimulated by the target neurons, or a unit responsive to the patient or clinician, can be coupled to the control unit or microdrive motor system. The measurement device, user, or clinician can indicate a response by the target muscles or other tissues to the stimulation or recording electrode(s) to further identify the target neurons and facilitate positioning of the stimulation electrode(s). For example, if the target neurons are directed to a muscle experiencing tremors, a measurement device can be used to observe the muscle and indicate changes in tremor frequency or amplitude in response to stimulation of neurons. Alternatively, the patient or clinician may observe the muscle and provide feedback.

The lead 110 for deep brain stimulation can include stimulation electrodes, recording electrodes, or both. In at least some embodiments, the lead 110 is rotatable so that the stimulation electrodes can be aligned with the target neurons after the neurons have been located using the recording electrodes.

Stimulation electrodes may be disposed on the circumference of the lead 110 to stimulate the target neurons. Stimulation electrodes may be ring-shaped so that current projects from each electrode equally in every direction from the position of the electrode along a length of the lead 110. Ring electrodes, however, typically do not enable stimulus current to be directed to only one side of the lead. Segmented electrodes, however, can be used to direct stimulus current to one side, or even a portion of one side, of the lead. When segmented electrodes are used in conjunction with an implantable pulse generator that delivers constant current stimulus, current steering can be achieved to more precisely deliver the stimulus to a position around an axis of the lead (i.e., radial positioning around the axis of the lead).

To achieve current steering, segmented electrodes can be utilized in additional to, or as an alternative to, ring electrodes. Though the following description discusses stimulation electrodes, it will be understood that all configurations of the stimulation electrodes discussed may be utilized in arranging recording electrodes as well.

Figure 2:
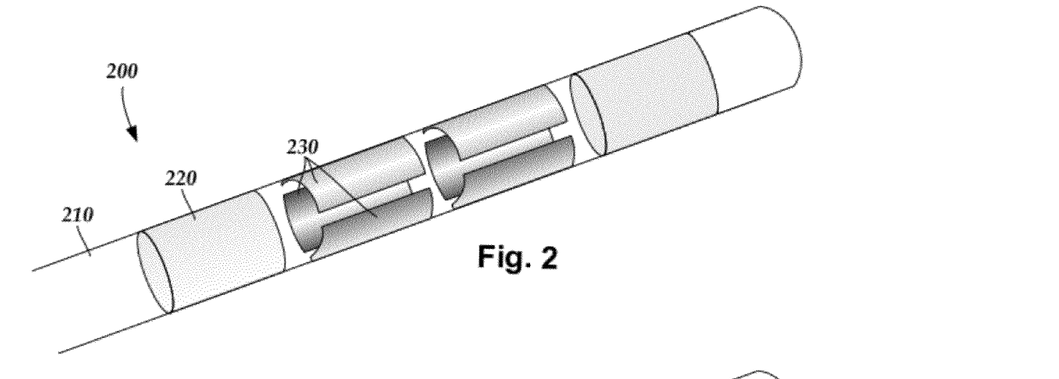
FIG. 2 is a schematic perspective view of one embodiment of a portion of a lead having a plurality of segmented electrodes, according to the invention.

FIG. 2 illustrates one embodiment of a distal portion of a lead 200 for brain stimulation. The lead 200 includes a lead body 210, one or more optional ring electrodes 220, and a plurality of sets of segmented electrodes 230. The lead body 210 can be formed of a biocompatible, non-conducting material such as, for example, a polymeric material. Suitable polymeric materials include, but are not limited to, silicone, polyurethane, polyethylene, polyurea, polyurethane-urea, or the like. Once implanted in the body, the lead 200 may be in contact with body tissue for extended periods of time. In at least some embodiments, the lead 200 has a cross-sectional diameter of no more than 1.5 mm and may be in the range of 1 to 1.5 mm. In at least some embodiments, the lead 200 has a length of at least 10 cm and the length of the lead 200 may be in the range of 25 to 70 cm.

The electrodes may be made using a metal, alloy, conductive oxide, or any other suitable conductive biocompatible material. Examples of suitable materials include, but are not limited to, platinum, platinum iridium alloy, iridium, titanium, tungsten, palladium, or the like. Preferably, the electrodes are made of a material that is biocompatible and does not substantially corrode under expected operating conditions in the operating environment for the expected duration of use.

Each of the electrodes can either be used or unused (OFF). When the electrode is used, the electrode can be used as an anode or cathode and carry anodic or cathodic current. In some instances, an electrode might be an anode for a period of time and a cathode for a period of time.

Stimulation electrodes in the form of ring electrodes 220 may be disposed on any part of the lead body 210, usually near a distal end of the lead 200. In FIG. 2, the lead 200 includes two ring electrodes 220. Any number of ring electrodes 220 may be disposed along the length of the lead body 210 including, for example, one, two three, four, five, six, seven, eight, nine, ten, eleven, twelve, thirteen, fourteen, fifteen, sixteen or more ring electrodes 220. It will be understood that any number of ring electrodes may be disposed along the length of the lead body 210. In some embodiments, the ring electrodes 220 are substantially cylindrical and wrap around the entire circumference of the lead body 210. In some embodiments, the outer diameters of the ring electrodes 220 are substantially equal to the outer diameter of the lead body 210. The length of the ring electrodes 220 may vary according to the desired treatment and the location of the target neurons. In some embodiments the length of the ring electrodes 220 are less than or equal to the diameters of the ring electrodes 220. In other embodiments, the lengths of the ring electrodes 220 are greater than the diameters of the ring electrodes 220.

Deep brain stimulation leads may include one or more sets of segmented electrodes. Segmented electrodes may provide for superior current steering than ring electrodes because target structures in deep brain stimulation are not typically symmetric about the axis of the distal electrode array. Instead, a target may be located on one side of a plane running through the axis of the lead. Through the use of a radially segmented electrode array ("RSEA"), current steering can be performed not only along a length of the lead but also around a circumference of the lead. This provides precise three-dimensional targeting and delivery of the current stimulus to neural target tissue, while potentially avoiding stimulation of other tissue.

In FIG. 2, the lead 200 is shown having a plurality of segmented electrodes 230. Any number of segmented electrodes 230 may be disposed on the lead body 210 including, for example, one, two three, four, five, six, seven, eight, nine, ten, eleven, twelve, thirteen, fourteen, fifteen, sixteen or more segmented electrodes 230. It will be understood that any number of segmented electrodes 230 may be disposed along the length of the lead body 210.

The segmented electrodes 230 may be grouped into sets of segmented electrodes, where each set is disposed around a circumference of the lead 200 at a particular longitudinal portion of the lead 200. The lead 200 may have any number segmented electrodes 230 in a given set of segmented electrodes. The lead 200 may have one, two, three, four, five, six, seven, eight, or more segmented electrodes 230 in a given set. In at least some embodiments, each set of segmented electrodes 230 of the lead 200 contains the same number of segmented electrodes 230. The segmented electrodes 230 disposed on the lead 200 may include a different number of electrodes than at least one other set of segmented electrodes 230 disposed on the lead 200.

The segmented electrodes 230 may vary in size and shape. In some embodiments, the segmented electrodes 230 are all of the same size, shape, diameter, width or area or any combination thereof. In some embodiments, the segmented electrodes 230 of each circumferential set (or even all segmented electrodes disposed on the lead 200) may be identical in size and shape.

Each set of segmented electrodes 230 may be disposed around the circumference of the lead body 210 to form a substantially cylindrical shape around the lead body 210. The spacing between individual electrodes of a given set of the segmented electrodes may be the same, or different from, the spacing between individual electrodes of another set of segmented electrodes on the lead 200. In at least some embodiments, equal spaces, gaps or cutouts are disposed between each segmented electrode 230 around the circumference of the lead body 210. In other embodiments, the spaces, gaps or cutouts between the segmented electrodes 230 may differ in size or shape. In other embodiments, the spaces, gaps, or cutouts between segmented electrodes 230 may be uniform for a particular set of the segmented electrodes 230, or for all sets of the segmented electrodes 230. The sets of segmented electrodes 230 may be positioned in irregular or regular intervals along a length the lead body 210.

Figure 6A:
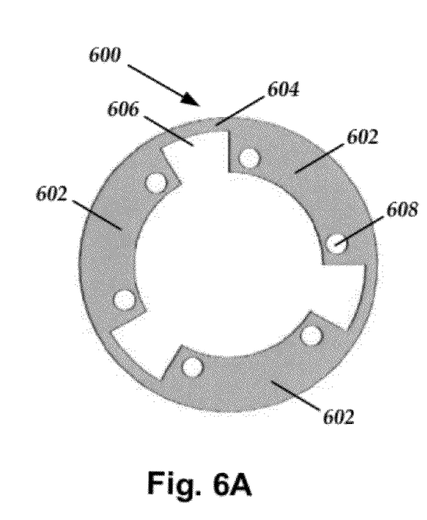
FIG. 6A is a schematic cross-sectional view of one embodiment of a pre-electrode having channels, according to the invention.

Conductor wires (see e.g., conductor wires 640 of FIG. 6) that attach to the ring electrodes 220 or segmented electrodes 230 extend along the lead body 210. These conductor wires may extend through the material of the lead 20 or along one or more lumens defined by the lead 200, or both. The conductor wires are presented at a connector (via terminals) for coupling of the electrodes 220, 230 to a control unit (not shown).

Figure 3A:
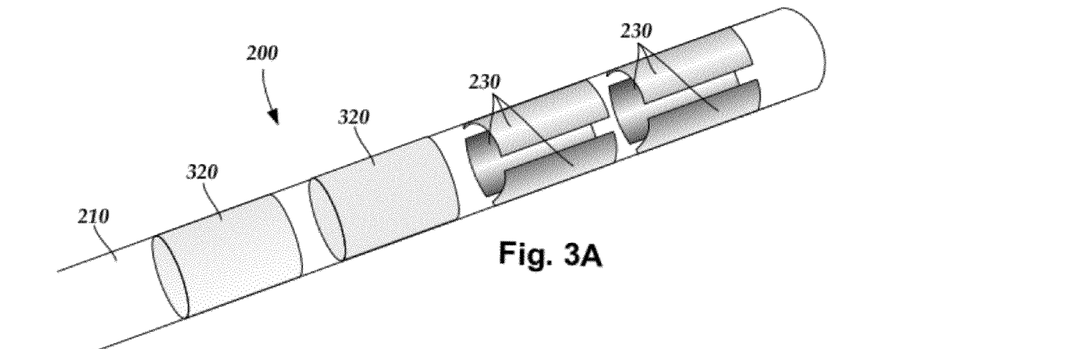
FIG. 3A is a perspective view of a third embodiment of a portion of a lead having a plurality of segmented electrodes, according to the invention.
Figure 3B:
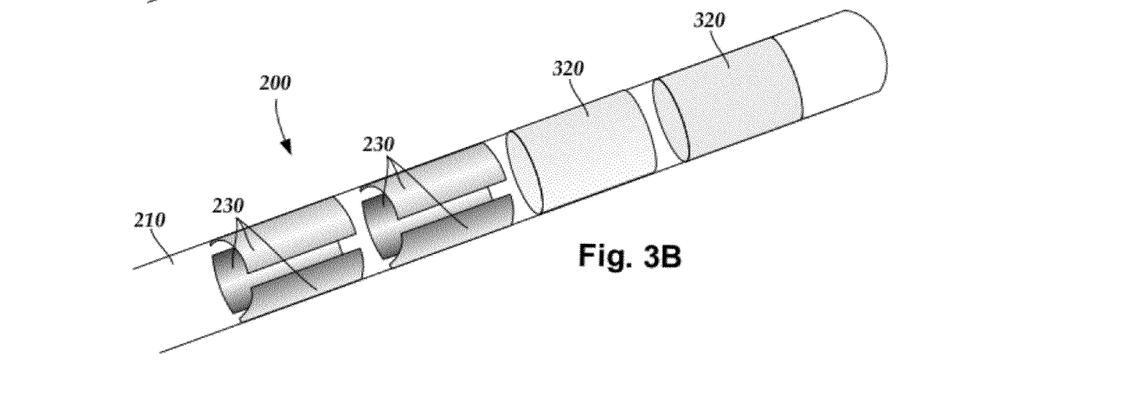
FIG. 3B is a perspective view of a fourth embodiment of a portion of a lead having a plurality of segmented electrodes, according to the invention.

When the lead 200 includes both ring electrodes 220 and segmented electrodes 230, the ring electrodes 220 and the segmented electrodes 230 may be arranged in any suitable configuration. For example, when the lead 200 includes two sets of ring electrodes 220 and two sets of segmented electrodes 230, the ring electrodes 220 can flank the two sets of segmented electrodes 230 (see e.g., FIG. 2). Alternately, the two sets of ring electrodes 220 can be disposed proximal to the two sets of segmented electrodes 230 (see e.g., FIG. 3A), or the two sets of ring electrodes 220 can be disposed distal to the two sets of segmented electrodes 230 (see e.g., FIG. 3B). It will be understood that other configurations are possible as well (e.g., alternating ring and segmented electrodes, or the like).

By varying the location of the segmented electrodes 230, different coverage of the target neurons may be selected. For example, the electrode arrangement of FIG. 3A may be useful if the physician anticipates that the neural target will be closer to a distal tip of the lead body 210, while the electrode arrangement of FIG. 3B may be useful if the physician anticipates that the neural target will be closer to a proximal end of the lead body 210.

Any combination of ring electrodes 220 and segmented electrodes 230 may be disposed on the lead 200. For example, the lead may include a first ring electrode 120, two sets of segmented electrodes, each set formed of three segmented electrodes 230, and a final ring electrode 120 at the end of the lead. This configuration may simply be referred to as a 1-3-3-1 configuration. It may be useful to refer to the electrodes with this shorthand notation. Thus, the embodiment of FIG. 3A may be referred to as a 1-1-3-3 configuration, while the embodiment of FIG. 3B may be referred to as a 3-3-1-1 configuration. Other eight-electrode configurations include, for example, a 2-2-2-2 configuration, where four sets of segmented electrodes are disposed on the lead, and a 4-4 configuration, where two sets of segmented electrodes, each having four segmented electrodes 230 are disposed on the lead. In some embodiments, the lead includes 16 electrodes. Possible configurations for a 16-electrode lead include, but are not limited to 4-4-4-4; 8-8; 3-3-3-3-3-1 (and all rearrangements of this configuration); and 2-2-2-2-2-2-2-2.

Figure 4:
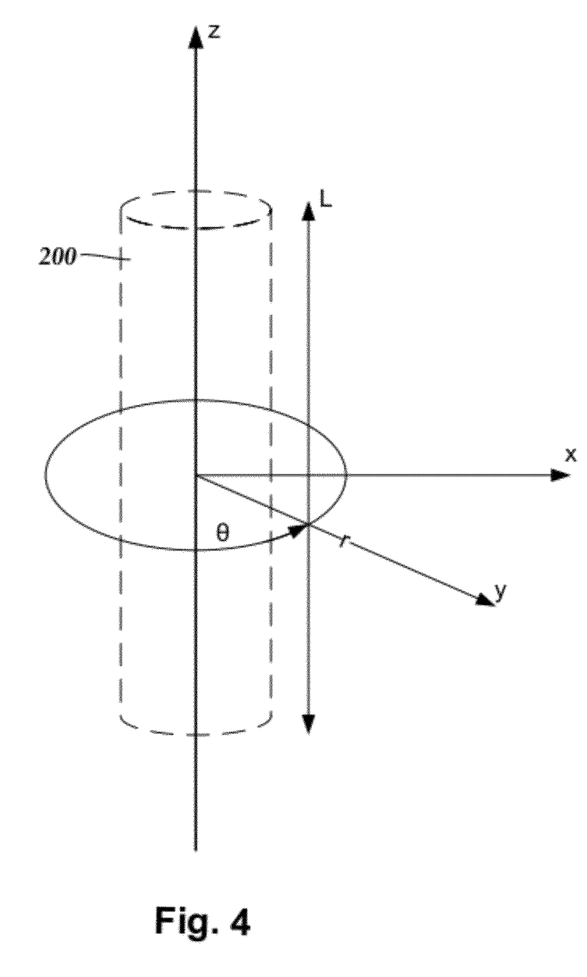
FIG. 4 is a schematic diagram of radial current steering along various electrode levels along the length of a lead, according to the invention.

FIG. 4 is a schematic diagram to illustrate radial current steering along various electrode levels along the length of the lead 200. While conventional lead configurations with ring electrodes are only able to steer current along the length of the lead (the z-axis), the segmented electrode configuration is capable of steering current in the x-axis, y-axis as well as the z-axis. Thus, the centroid of stimulation may be steered in any direction in the three-dimensional space surrounding the lead 200. In some embodiments, the radial distance, r, and the angle $\theta$ around the circumference of the lead 200 may be dictated by the percentage of anodic current (recognizing that stimulation predominantly occurs near the cathode, although strong anodes may cause stimulation as well) introduced to each electrode. In at least some embodiments, the configuration of anodes and cathodes along the segmented electrodes allows the centroid of stimulation to be shifted to a variety of different locations along the lead 200.

As can be appreciated from FIG. 4, the centroid of stimulation can be shifted at each level along the length of the lead 200. The use of multiple sets of segmented electrodes at different levels along the length of the lead allows for three-dimensional current steering. In some embodiments, the sets of segmented electrodes are shifted collectively (i.e., the centroid of simulation is similar at each level along the length of the lead). In at least some other embodiments, each set of segmented electrodes is controlled independently. Each set of segmented electrodes may contain two, three, four, five, six, seven, eight or more segmented electrodes. It will be understood that different stimulation profiles may be produced by varying the number of segmented electrodes at each level. For example, when each set of segmented electrodes includes only two segmented electrodes, uniformly distributed gaps (inability to stimulate selectively) may be formed in the stimulation profile. In some embodiments, at least three segmented electrodes 230 in a set are utilized to allow for true 360° selectivity.

As previously indicated, the foregoing configurations may also be used while utilizing recording electrodes. In some embodiments, measurement devices coupled to the muscles or other tissues stimulated by the target neurons or a unit responsive to the patient or clinician can be coupled to the control unit or microdrive motor system. The measurement device, user, or clinician can indicate a response by the target muscles or other tissues to the stimulation or recording electrodes to further identify the target neurons and facilitate positioning of the stimulation electrodes. For example, if the target neurons are directed to a muscle experiencing tremors, a measurement device can be used to observe the muscle and indicate changes in tremor frequency or amplitude in response to stimulation of neurons. Alternatively, the patient or clinician may observe the muscle and provide feedback.

The reliability and durability of the lead will depend heavily on the design and method of manufacture. Fabrication techniques discussed below provide methods that can produce manufacturable and reliable leads.

When the lead 200 includes a plurality of sets of segmented electrodes 230, it may be desirable to form the lead 200 such that corresponding electrodes of different sets of segmented electrodes 230 are radially aligned with one another along the length of the lead 200 (see e.g., the segmented electrodes 230 shown in FIG. 2). Radial alignment between corresponding electrodes of different sets of segmented electrodes 230 along the length of the lead 200 may reduce uncertainty as to the location or orientation between corresponding segmented electrodes of different sets of segmented electrodes. Accordingly, it may be beneficial to form electrode arrays such that corresponding electrodes of different sets of segmented electrodes along the length of the lead 200 are radially aligned with one another and do not radially shift in relation to one another during manufacturing of the lead 200.

Figure 5:
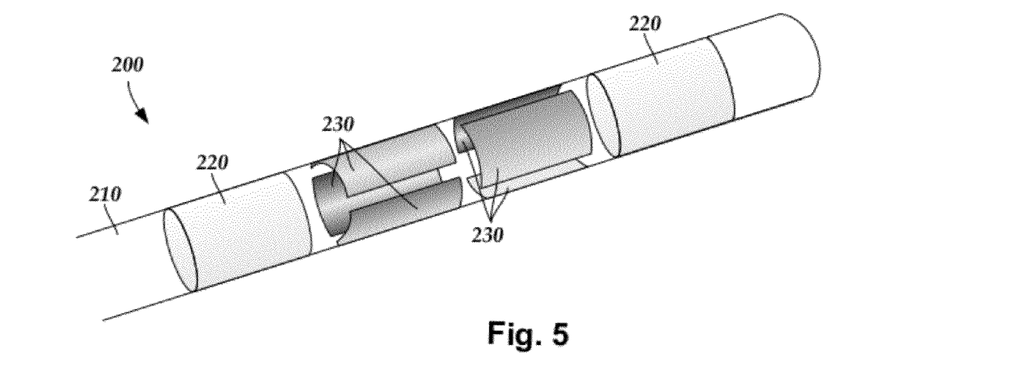
FIG. 5 is a schematic perspective view of another embodiment of a portion of a lead having a plurality of segmented electrodes arranged in a staggered orientation, according to the invention.

FIG. 5 is a side view of another embodiment of the lead 200 having a plurality of sets of segmented electrodes. As shown in FIG. 5, individual electrodes in the two sets of segmented electrodes 230 are staggered relative to one another along the length of the lead body 210. In some cases, the staggered positioning of corresponding electrodes of different sets of segmented electrodes along the length of the lead 200 may be designed for a specific application.

A number of issues can arise in the manufacture of leads containing segmented electrodes. For example, it may be difficult to maintain the position and spacing between segmented electrodes during or after manufacture, particularly during operations in which parts of the lead body are heated for reflow. The segmented electrodes may shift within the heated polymer, altering the spacing between segmented electrodes. Furthermore, electrode retention after manufacture may be of concern. Segmented electrodes and methods of manufacture can be designed to address these and other issues. For example, U.S. Provisional Patent Application Ser. No. 61/356,529, incorporated herein by reference, provides some examples of segmented electrodes and method of manufacture.

In at least some embodiments, the segmented electrode can include features that facilitate retention and maintenance of position and spacing during or after (or both during and after) manufacture. For example, the segmented electrode can include at least one channel formed in the segmented electrode and extending from a proximal end to the distal end of a segmented electrode. During manufacture, the channel can be at least partially filled (preferably, completely filled) with material from the lead body or other portions of the lead to facilitate maintenance of the position and spacing, as well as retention, of the segmented electrode.

FIGS. 6A-6F illustrate, in cross-section, several different embodiments of a pre-electrode 600. The pre-electrode is used to form a set of radially-disposed segmented electrodes. The pre-electrode may be formed of a conductor such as a metal, alloy, conductive oxide, or any other suitable conductive material. In some embodiments, the pre-electrode 600 is formed of platinum, platinum-iridium, iridium, 616L stainless steel (or any other suitable stainless steel), tantalum, nitinol, iridium rhodium, or a conductive polymer. The pre-electrode 600 includes individual segmented electrodes 602 joined by connecting material 604. The connecting material 604 can be removed (for example, by grinding, machining, etching, ablating, or otherwise removing the connecting material 604) to leave the separated segmented electrodes 602 when the pre-electrode is in place on the lead. The pre-electrode 600 defines cutouts 606 between the individual segmented electrodes, which typically define the spacing between the segmented electrodes of a particular set of segmented electrodes. The connecting material 604 may correspond only to the material between the segmented electrodes 602 or may include other portions of the pre-electrode 600 (e.g., an outer ring of material that can be ground away to release the underlying segmented electrodes).

The pre-electrode 600 may be formed in the shape of a disk or ring or any other suitable shape. In some embodiments, the pre-electrode 600 is formed of a substantially cylindrical member having a diameter larger than the desired final diameter of the lead. A cylindrical lead may be obtained by grinding (e.g., centerless grinding), machining, etching, or ablating the outer diameter of the pre-electrode 600. The grinding can also release the individual segmented electrodes. The pre-electrodes in FIGS. 6A-6F illustrate embodiments with three segmented electrodes, but it will be recognized that other embodiments of a pre-electrode can have two, four, five, six, seven, eight, or more segmented electrodes.

The pre-electrode 600 further includes one or more channels 608 formed in the segmented electrodes 602. Preferably, there is at least one channel 608 formed in each of the segmented electrodes 602. There may be two, three, four, or more channels formed in each of the segmented electrodes. The number of channels in each segmented electrode may be the same or different from the number of channels in other segmented electrodes. These channels can allow material, such as material from the lead body (including spacers positioned, for example, between sets of segmented electrodes or between a set of segmented electrodes and a ring electrode) or other material, to be placed, or flowed, into the channels. The material within the channels can facilitate maintenance of the position and spacing, as well as retention, of the segmented electrode.

FIG. 6A illustrates one embodiment in which the channels 608 have a circular cross-sectional shape and the channels are surrounded by the segmented electrode. It will be recognized that other embodiments, similar to those illustrated in FIG. 6A, could include channels with other regular or irregular cross-sectional shapes including, but not limited to, triangular, oval, square, rectangular, pentagonal, hexagonal, octagonal, "T"-shaped, "L"-shaped, and other cross-sectional shapes. It will be recognized that the cross-sectional shape of the channel need not be uniform along the length of the channel. It will be further recognized that the channels need not be identical and that different segmented electrodes may have differently shaped channels or that channels in a particular segmented electrode may be differently shaped. In some embodiments, the channels do not extend fully through the segmented electrode, but only extend partially (e.g., one half or one third of the distance) through the segmented electrode. In such embodiments, two channels may extend towards each other from opposing sides of the segmented electrode.

Figure 6B:
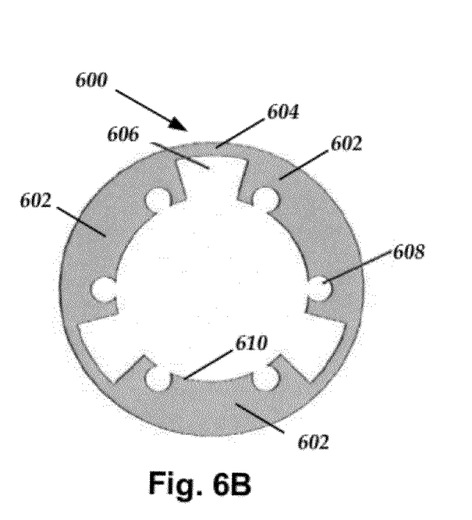
FIG. 6B is a schematic cross-sectional view of a second embodiment of a pre-electrode having channels, according to the invention.
Figure 6C:
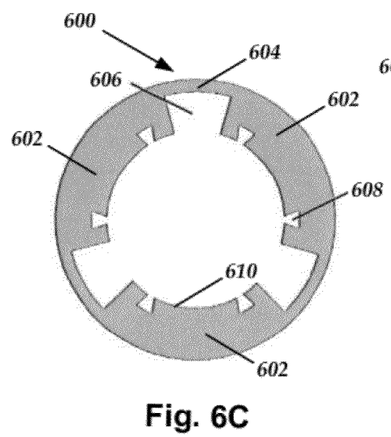
FIG. 6C is a schematic cross-sectional view of a third embodiment of a pre-electrode having channels, according to the invention.
Figure 6D:
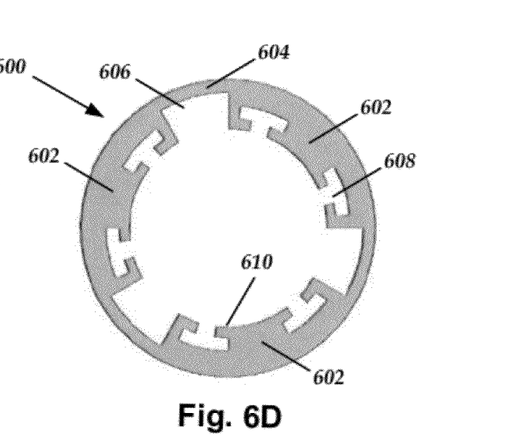
FIG. 6D is a schematic cross-sectional view of a fourth embodiment of a pre-electrode having channels, according to the invention.

In other embodiments, the channels 608 are open along at least part of the width of the segmented electrodes 602, particularly along the interior surface 610 of the segmented electrodes. These channels may be considered grooves or notches in an interior surface of the segmented electrodes. FIG. 6B illustrates one embodiment in which the channels 608 are open along the interior surface 610 of the segmented electrodes 602. These channels have a circular cross-sectional shape. FIG. 6C illustrates another embodiment in which the channels 608 are open along the interior surface 610 of the segmented electrodes 602. These channels have a trapezoidal cross-sectional shape. FIG. 6D illustrates yet another embodiment in which the channels 608 have a 'T' cross-sectional shape and are open at the interior surface 610 of the segmented electrodes 602.

It will be recognized that other embodiments, similar to those illustrated in FIGS. 6B, 6C, and 6D, could include channels with other regular or irregular cross-sectional shapes including, but not limited to, triangular, oval, square, rectangular, pentagonal, hexagonal, octagonal, "L"-shaped, and other cross-sectional shapes. It will be recognized that the cross-sectional shape of the channel need not be uniform along the length of the channel or that the channel need not be open along its entire length. It will be further recognized that the channels need not be identical and that different segmented electrodes may have differently shaped channels or that channels in a particular segmented electrode may be differently shaped.

Figure 6E:
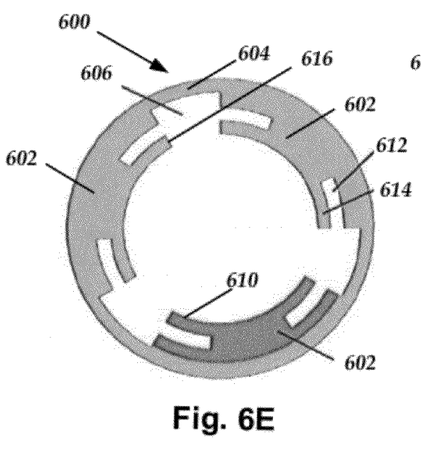
FIG. 6E is a schematic cross-sectional view of one embodiment of a pre-electrode having notches and flanges, according to the invention.

FIGS. 6E and 6F illustrate embodiments that use notches 612 and flanges 614 to provide retention features. In the embodiment illustrated in FIG. 6E, the segmented electrodes 602 have an "I" shape (outlined for the bottom segmented electrode in FIG. 6E). Each segmented electrode 602 includes at least one notch 612 extending into the segmented electrode from one of the lateral side surfaces 616 of the segmented electrode. The notch 612 preferably extends from the distal end of the segmented electrode to the proximal end. Preferably, there is at least one notch 612 extending into the segmented electrode 602 from each of the lateral side surfaces 616. Each notch 612 defines a flange 614 between the notch and the interior surface 610 of the segmented electrode.

Figure 6F:
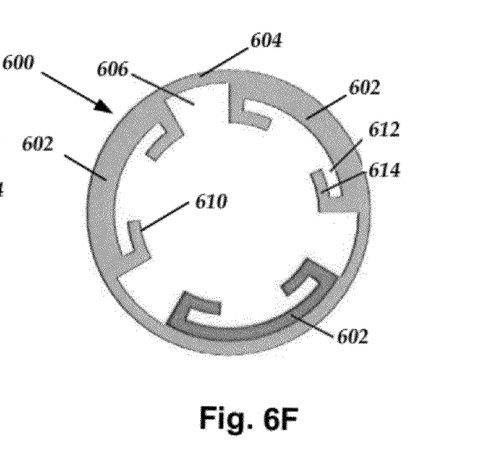
FIG. 6F is a schematic cross-sectional view of a second embodiment of a pre-electrode having notches and flanges, according to the invention.

In the embodiment illustrated in FIG. 6F, the segmented electrodes 602 have a "C" shape (outlined for the bottom segmented electrode in FIG. 6F). Each segmented electrode 602 includes at least one notch 612 extending away from a center of the segmented electrode toward one of the lateral side surfaces 616. The notch 612 preferably extends from the distal end of the segmented electrode to the proximal end. Preferably, there is at least one notch 612 extending toward each of the lateral side surfaces 616 of the segmented electrode 602. The opening formed by the notches is also open at the interior surface 610 of the segmented electrode. Each notch 612 defines a flange 614 between the notch and the interior surface 610 of the segmented electrode. In some embodiments, the flanges may appear to be more rounded or hook-shaped than those illustrated in FIG. 6F.

These notches can allow material, such as material from the lead body (including spacers positioned, for example, between sets of segmented electrodes or between a set of segmented electrodes and a ring electrode) or other material, to be placed, or flowed, into the notches. This material can facilitate maintenance of the position and spacing, as well as retention, of the segmented electrode. It will be recognized that the notches and flanges need not be identical and that different segmented electrodes may have differently shaped notches and flanges or that notches or flanges in a particular segmented electrode may be differently shaped.

Figure 7A:
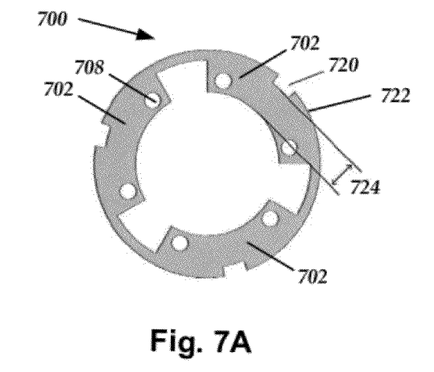
FIG. 7A is a schematic cross-sectional view of one embodiment of a pre-electrode having grooves in the exterior surface of the pre-electrode, according to the invention.
Figure 7B:
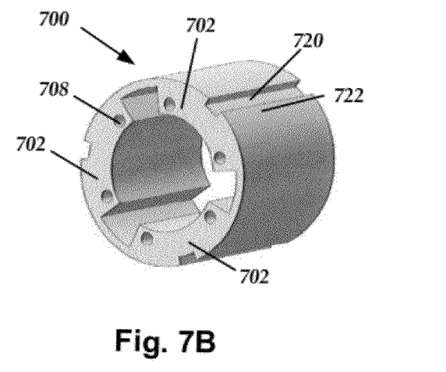
FIG. 7B is a schematic perspective view of the pre-electrode assembly of FIG. 7A, according to the invention.

In some embodiments, a pre-electrode may have one or more grooves formed on the exterior surface of the pre-electrode. In at least some embodiments, a groove on the exterior surface of the pre-electrode is aligned with one of the segmented electrodes. FIGS. 7A and 7B illustrate one embodiment of a pre-electrode 700 with one or more grooves 720 formed on the exterior surface 722 of the pre-electrode. The pre-electrode 700 also includes segmented electrodes 702 and optional channels 708 in the segmented electrodes. It will be understood that any of the channels, notches, or flanges described above can be used with this pre-electrode.

One or more of the grooves 720 may be aligned individually with a segmented electrode. The grooves 720 may be used to mark the exterior surface of the pre-electrode to indicate the position of a segmented electrode beneath to facilitate manufacture and orientation of the pre-electrode in the desired position during manufacture. Such grooves 720 may facilitate aligning several pre-electrodes 700 so that the underlying segmented electrodes will have the proper relative positions after completion of the manufacture of the lead. In at least some embodiments, the grooves extend parallel to a longitudinal axis of the pre-electrode, as illustrated in FIGS. 7A and 7B.

The grooves 720 may also provide an area for welding a conductor to a segmented electrode. Additionally or alternatively, the grooves 720 may be used to reduce the local wall thickness 724 of the pre-electrode to facilitate welding (e.g., by reducing the thermal mass at the point of welding.)

In some embodiments, the groove 720 does not extend into the segmented electrode 702, so that when the connecting material of the pre-electrode 700 is removed by, for example, grinding, to release the individual segmented electrodes, the groove is no longer visible. In other embodiments, the groove 720 does extend into the segmented electrode 702 and may be used to mark the segmented electrode.

Figure 8A:
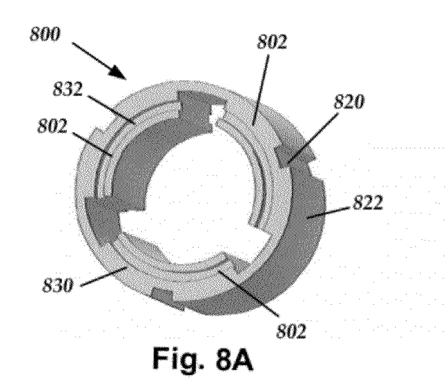
FIG. 8A is a schematic perspective view of one embodiment of a pre-electrode with an arcuate groove in a distal or proximal end of the pre-electrode, according to the invention.
Figure 8B:
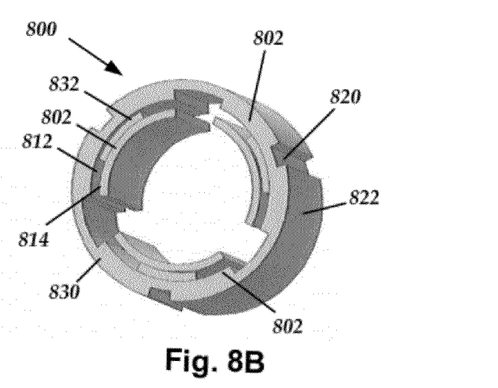
FIG. 8B is a schematic perspective view of a second embodiment of a pre-electrode with an arcuate groove in a distal or proximal end of the pre-electrode, according to the invention.

Arcuate grooves in the proximal end, distal end, or both ends of the segmented electrodes can also act as retention features. FIGS. 8A and 8B illustrated two embodiments of a pre-electrode 800 with arcuate grooves 830 on a distal or proximal end 832 (or both) of the segmented electrodes 802 of the pre-electrode. FIG. 8A illustrates an embodiment which also includes optional grooves 820 in the exterior surface 822 of the pre-electrode 800. FIG. 8B illustrates an embodiment that further includes notches 812 and flanges 814 similar to those in the pre-electrode embodiment of FIG. 6E. It will be understood that any of the other channels, notches, or flanges described above can be used in conjunction with the arcuate grooves.

These arcuate grooves 830 can allow material, such as material from the lead body (including spacers positioned, for example, between sets of segmented electrodes or between a set of segmented electrodes and a ring electrode) or other material, to be placed, or flowed, into the arcuate grooves. This material can facilitate maintenance of the position and spacing, as well as retention, of the segmented electrode. It will be recognized that the arcuate grooves need not be identical and that different segmented electrodes may have differently shaped arcuate grooves.

Leads can be formed by a variety of methods. In some embodiments of the method of manufacturing a lead with segmented electrodes having channels, notches, grooves, or cutouts, material can be introduced into the channel, notch, groove, or cutout and then reflowed to facilitate maintenance of the position and spacing, as well as retention, of the segmented electrode. FIGS. 9A-9H illustrate one embodiment of a suitable method.

Figure 9A:
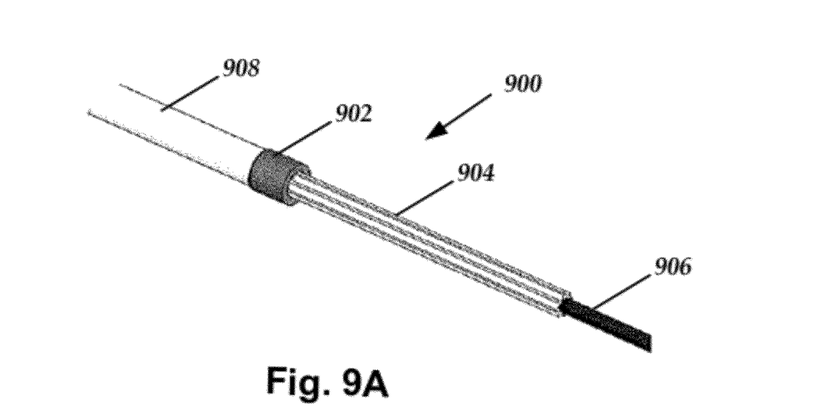
FIG. 9A is a schematic perspective view of a portion of a lead body with a ring electrode disposed thereon in one embodiment of a method of making a lead, according to the invention.

FIG. 9A illustrates a distal end of a lead 900 with one ring electrode 902 disposed on a conductor carrier 904 and a mandrel 906 disposed in the conductor carrier 904. A portion of a lead body 908 is also illustrated. The conductor carrier 904 provides one or more lumens through which the conductors (not shown) are carried along the lead from the terminals (not shown) at a proximal end of the lead to the electrodes at the distal end of the lead. Each lumen can be opened (e.g., ablated to form an opening) at a particular point to allow the conductor carried within the lumen to be attached to a corresponding electrode. The lead body 908 can be formed of a biocompatible, non-conducting material such as, for example, a polymeric material. Suitable polymeric materials include, but are not limited to, silicone, polyurethane, polyethylene, polyurea, polyurethane-urea, or the like.

Figure 9B:
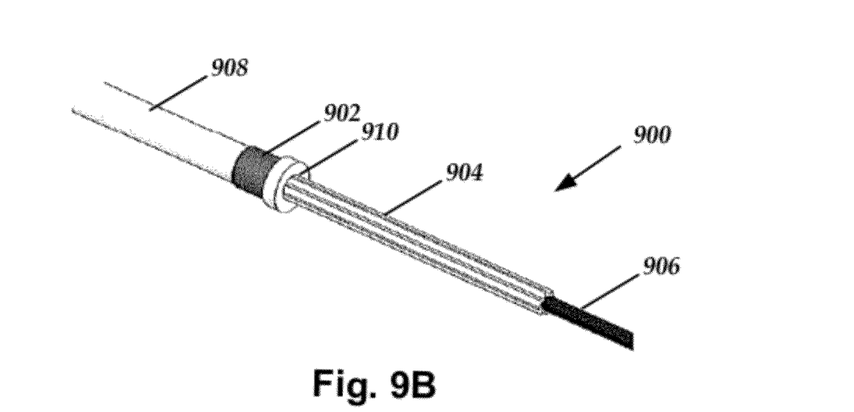
FIG. 9B is a schematic perspective view of a portion of a lead body with a ring electrode and spacer disposed thereon in one embodiment of a method of making a lead, according to the invention.

A non-conductive spacer 910 can then be added to the lead assembly next to the ring electrode 902, as illustrated in FIG. 9B. The spacer 910 can be formed of a biocompatible, non-conducting material such as, for example, a polymeric material. Suitable polymeric materials include, but are not limited to, silicone, polyurethane, polyethylene, polyurea, polyurethane-urea, or the like. The spacer 910 can be made of the same or different non-conductive material as the lead body 908.

Figure 9C:
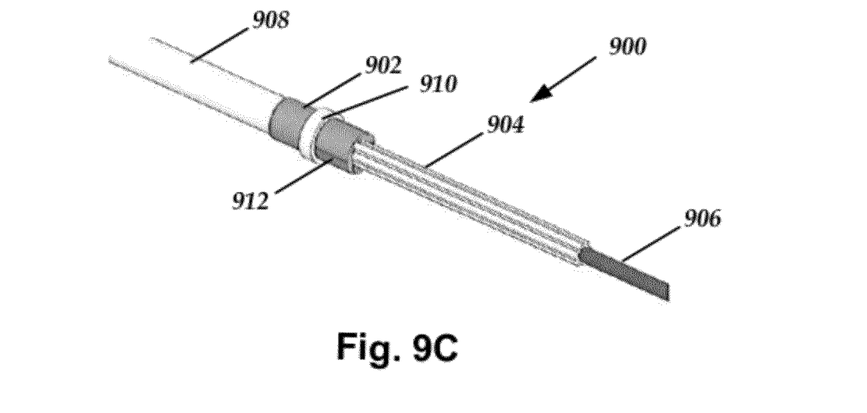
FIG. 9C is a schematic perspective view of a portion of a lead body with a ring electrode, spacer, and pre-electrode disposed thereon in one embodiment of a method of making a lead, according to the invention.
Figure 9D:
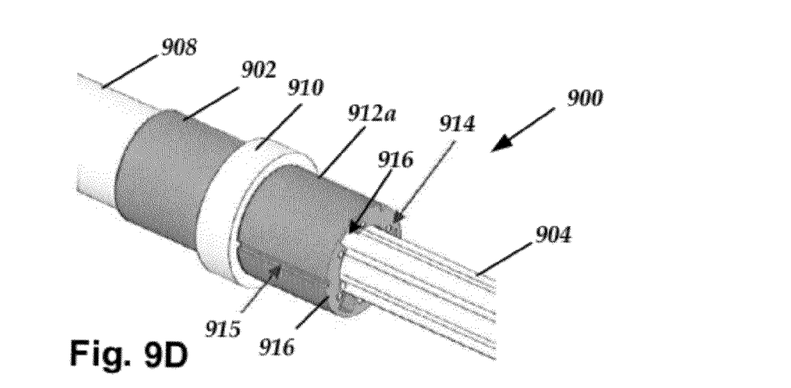
FIG. 9D is a schematic perspective view of a portion of a lead body with a ring electrode, spacer, and pre-electrode disposed thereon in one embodiment of a method of making a lead, according to the invention.

A pre-electrode 912 is added to the lead assembly next to the spacer 910, as illustrated in FIG. 9C. The pre-electrode 912 can be, for example, any of the embodiments described above or a variation thereof. FIG. 9D illustrates a pre-electrode 912a which corresponds to the embodiment of FIG. 7A. This pre-electrode 912a includes cylindrical channels 914 formed through each of the segmented electrodes 916, cutouts 918 between the segmented electrodes, and grooves 915 formed in the exterior surface of the pre-electrode.

Figure 9E:
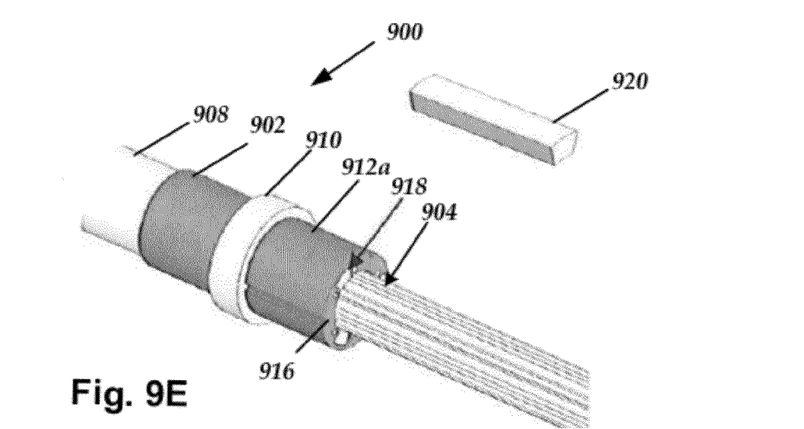
FIG. 9E is a schematic perspective view of a portion of a lead body with a ring electrode, spacer, and pre-electrode disposed thereon and non-conductive material for insertion in openings in the pre-electrode in one embodiment of a method of making a lead, according to the invention.

Non-conductive material 920 is inserted into the channels 914 and optionally into the cutouts 918, as illustrated in FIG. 9E. The non-conductive material 920 is preferably a reflowable polymer material and may be the same material as the material of the lead body 908, the material of the spacer 910, or both. The non-conductive material 920 can be formed of a biocompatible, non-conducting material such as, for example, a polymeric material. Suitable polymeric materials include, but are not limited to, silicone, polyurethane, polyethylene, polyurea, polyurethane-urea, or the like. The non-conductive material may take any suitable form including monofilament, shaped inter-segment fillers, and the like. It will be recognized that non-conductive material can be placed in the channels of any of the pre-electrodes of FIGS. 9A-9D, the notches of the pre-electrodes of FIGS. 9E and 9F, and the arcuate grooves of the pre-electrodes of FIGS. 8A and 8B.

Figure 10A:
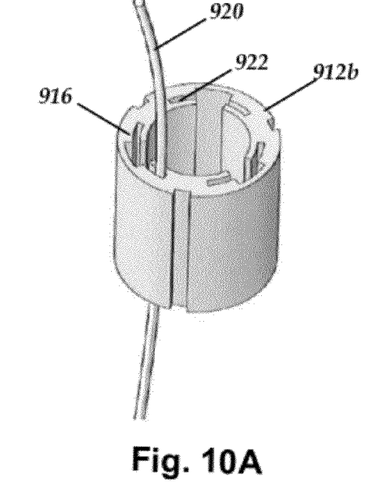
FIG. 10A is a schematic perspective view of one embodiment of a pre-electrode with non-conductive material inserted in notches of the pre-electrode, according to the invention.
Figure 10B:
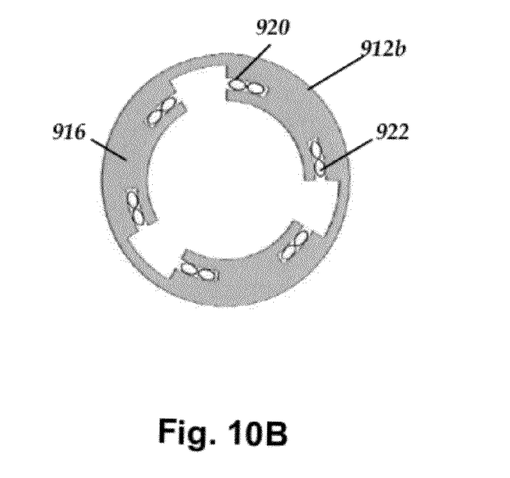
FIG. 10B is a schematic cross-sections view of the pre-electrode assembly of FIG. 10A, according to the invention.

FIGS. 10A and 10B illustrate another embodiment using a pre-electrode 912b that is similar to the pre-electrode of FIG. 6E. In this particular embodiment, non-conductive material 920 is inserted into the notches 922 in the segmented electrodes 916 of the pre-electrode 912b. As illustrated in FIG. 10B, this non-conductive material may take the form of two strands of monofilament. It will be understood that other forms of non-conductive material may also be used.

Figure 9F:
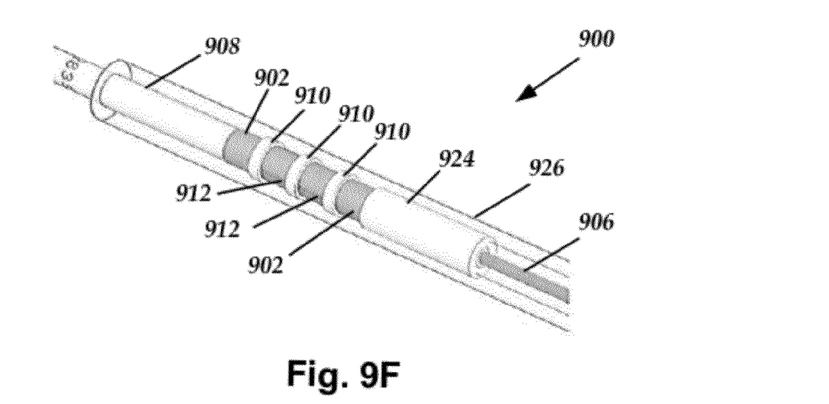
FIG. 9F is a schematic perspective view of a portion of a lead body with a tubing formed over the lead body, electrodes, and spacers in one embodiment of a method of making a lead, according to the invention.

The process of adding spacers and pre-electrodes or ring electrodes is repeated until all of the pre-electrodes and ring electrodes are added to the lead, as illustrated in FIG. 9F. It will be recognized that any arrangement of pre-electrodes and ring electrodes (including arrangements with no ring electrodes) can be formed.

A terminal portion 924 of the lead body is then added, as illustrated in FIG. 9F and tubing 926 is placed over the distal portion of the lead, including the electrodes and spacers. The polymeric components (i.e., spacers 910, the non-conductive material 920, and optionally the lead body 908 and terminal portion 924 of the lead body) are reflowed. During the reflow process, the non-conductive material 920 bonds with the spacers 910, and optionally the lead body 908 and terminal portion 924, to facilitate retention of the segmented electrodes 916 in the lead.

Figure 9G:
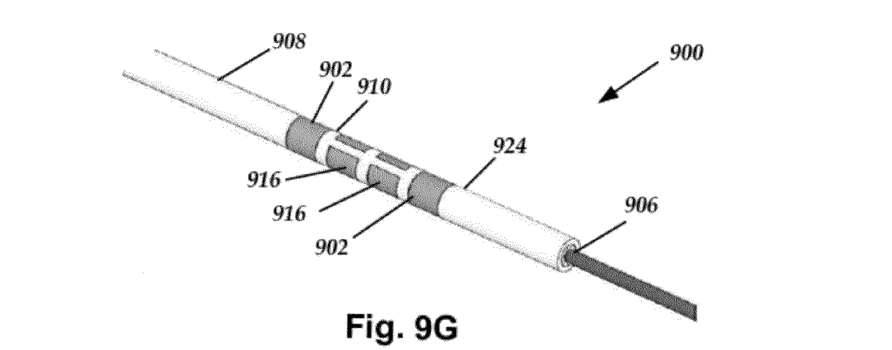
FIG. 9G is a schematic perspective view of a lead body in which the pre-electrodes have been ground to release segmented electrodes in one embodiment of a method of making a lead, according to the invention.
Figure 9H:
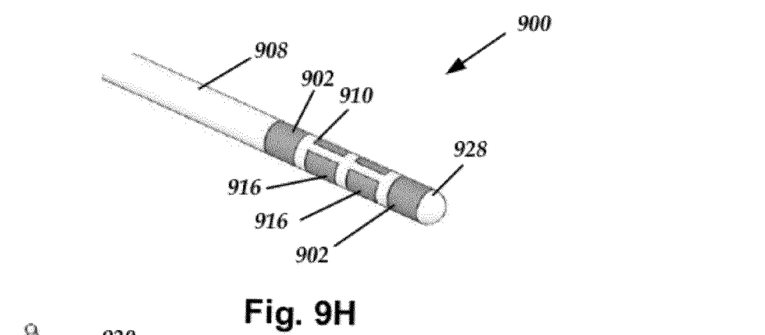
FIG. 9H is a schematic perspective view of a portion of a lead in one embodiment of a method of making a lead, according to the invention.

The distal portion of the lead is then ground down to the desired outer diameter which also separates the segmented electrodes, as illustrated in FIG. 9G. It will be recognized that methods other than grinding can be used to separate the segmented electrodes, as described above. The mandrel is removed and the distal end of the lead is formed into tip 928, as illustrated in FIG. 9H. The manufacturing process provides segmented electrodes which are retained within the lead by material formed in channels within the segmented electrodes.

The above specification, examples, and data provide a description of the manufacture and use of the composition of the invention. Since many embodiments of the invention can be made without departing from the spirit and scope of the invention, the invention also resides in the claims hereinafter appended.

What is claimed as new and desired to be protected by Letters Patent of the United States is:

1. A stimulation lead, comprising:
    a lead body comprising a longitudinal surface, a distal end, and a proximal end, wherein the lead body comprises a material that is biocompatible, non-conducting, and polymeric; and
    a plurality of electrodes disposed along the longitudinal surface of the lead body near the distal end of the lead body, the plurality of electrodes comprising a plurality of segmented electrodes, each of the segmented electrodes comprising an exterior surface, an interior surface opposite the exterior surface, a proximal end, and a distal end, at least one of the segmented electrodes comprising at least one channel formed in the segmented electrode and extending from the proximal end to the distal end of the segmented electrode, wherein a portion of the material of the lead body is disposed in the at least one channel of the at least one of the segmented electrodes to facilitate retention of the at least one of the segmented electrodes in the lead body.

2. The stimulation lead of claim 1, wherein the channel is open along the interior surface.

3. The stimulation lead of claim 1, wherein the channel has a circular cross-section.

4. The stimulation lead of claim 1, wherein the channel has a trapezoidal or triangular cross-section.

5. The stimulation lead of claim 1, wherein the channel has a T-shaped or L-shaped cross-section.

6. The stimulation lead of claim 1, wherein each segmented electrodes comprises at least one channel formed in the segmented electrode and extending from the proximal end to the distal end of the segmented electrode.

7. The stimulation lead of claim 1, wherein the at least one channel is a plurality of channels.

8. The stimulation lead of claim 1, wherein at least one of the segmented electrodes comprises a groove formed in the exterior surface and extending from the proximal end to the distal end of the segmented electrode.

9. The stimulation lead of claim 1, wherein each segmented electrode further comprises a distal end surface and a proximal end surface, wherein at least one segmented electrode comprises an arcuate groove formed in at least one of the distal end surface or the proximal end surface.

10. A stimulation lead, comprising:
    a lead body comprising a longitudinal surface, a distal end, and a proximal end, wherein the lead body comprises a material that is biocompatible, non-conducting, and polymeric; and
    a plurality of electrodes disposed along the longitudinal surface of the lead body near the distal end of the lead body, the plurality of electrodes comprising a plurality of segmented electrodes, each of the segmented electrodes comprising an exterior surface exposed for stimulating adjacent tissue, an interior surface opposite the exterior surface, a proximal end, and a distal end, at least one of the segmented electrodes comprising an arcuate groove formed in, and extending circumferentially along, at least one of a surface of the distal end or a surface of the proximal end, wherein the arcuate groove is spaced apart from the exterior surface of the segmented electrode, wherein a portion of the material of the lead body is disposed in the arcuate groove of the at least one of the segmented electrodes to facilitate retention of the at least one of the segmented electrodes in the lead body.

11. The stimulation lead of claim 10, wherein the at least one of the segmented electrodes comprises arcuate grooves formed in both the distal end surface and the proximal end surface.

12. The stimulation lead of claim 10, wherein the at least one of the segmented electrodes further comprises at least one notch formed in the segmented electrode and extending from the proximal end to the distal end of the segmented electrode.

13. A stimulation lead, comprising:
   a lead body comprising a longitudinal surface, a distal end, and a proximal end, wherein the lead body comprises a material that is biocompatible, non-conducting, and polymeric; and
   a plurality of electrodes disposed along the longitudinal surface of the lead body near the distal end of the lead body, the plurality of electrodes comprising a plurality of segmented electrodes, each of the segmented electrodes comprising an exterior surface, an interior surface opposite the exterior surface, a proximal end, and a distal end, at least one of the segmented electrodes comprising a notch formed in the segmented electrode and extending from the proximal end to the distal end of the segmented electrode, wherein a portion of the material of the lead body is disposed in the notch of the at least one of the segmented electrodes to facilitate retention of the at least one of the segmented electrodes in the lead body.

14. The stimulation lead of claim 13, wherein the notch extends from a lateral surface of the segmented electrode inward toward a center of the segmented electrode.

15. The stimulation lead of claim 13, wherein the notch extends from a center of the segmented electrode outward toward a lateral surface of the segmented electrode.

16. The stimulation lead of claim 13, wherein the at least one of the segmented electrodes comprises two notches.

* * * * *